United States Patent

Mistry et al.

Patent Number: 5,099,071
Date of Patent: Mar. 24, 1992

[54] ANTHANTHRONE DERIVATIVES

[75] Inventors: Pralad Mistry, Ashton-under-Lyne; Prakash Patel, Edgerton, both of England

[73] Assignee: Imperial Chemical Industries PLC, London, England

[21] Appl. No.: 608,398

[22] Filed: Nov. 2, 1990

[30] Foreign Application Priority Data

Nov. 9, 1989 [GB] United Kingdom ............... 8925362

[51] Int. Cl.$^5$ ............................................. C07C 321/30
[52] U.S. Cl. ..................................... 568/42; 546/153; 568/43
[58] Field of Search ...................... 546/153; 568/42, 43

[56] References Cited

FOREIGN PATENT DOCUMENTS 1308796 10/1962 European Pat. Off. .
452755 5/1968 European Pat. Off. .

OTHER PUBLICATIONS

Chemical Abstracts, vol. 59, 791b, 1962.
Chemical Abstracts, vol. 58, 14161d, 1962.
Chemical Index, entry 2827-74-9, (1965-1971).

Primary Examiner—Mary C. Lee
Assistant Examiner—Lenora Miltenberger
Attorney, Agent, or Firm—Cushman, Darby & Cushman

[57] ABSTRACT

A charge generating compound for use in electrophotographic devices of the formula:

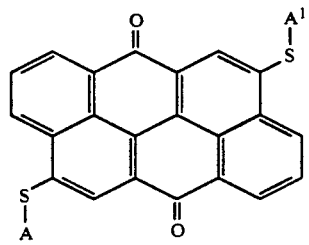

wherein:

A and $A^1$ are each independently selected from phenyl, substituted phenyl, quinolino, naphthyl and substituted naphthyl wherein the substituents are independently selected from halo, alkyl, alkoxy, alkylthio, phenyl, phenoxy, phenylthio, $CF_3$, $CH_2OH$, $CO_2R^1$, $NHCOR^1$, $COR^1$, $NO_2$ and $NR^1R^2$;

$R^1$ and $R^2$ are each independently H or $C_{1-6}$-alkyl.

5 Claims, No Drawings

ANTHANTHRONE DERIVATIVES

This invention relates to a novel anthanthrone compound which may be used as a charge generating compound (CGC) in the photosensitive elements of an electrophotographic device such as a copier or printer.

According to the present invention there is provided a compound of general Formula (1):

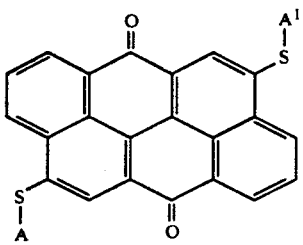

wherein:
A and $A^1$ are each independently selected from phenyl, substituted phenyl, quinolino, naphthyl and substituted naphthyl wherein the substituents are independently selected from halo, alkyl, alkoxy, alkylthio, phenyl, phenoxy, phenylthio, $CF_3$, $CH_2OH$, $CO_2R^1$, $NHCOR^1$, $COR^1$, $NO_2$ and $NR^1R^2$;
$R^1$ and $R^2$ are each independently H or $—C_{1-6}$-alkyl.

It is preferred that A and $A^1$ are each independently phenyl or naphthyl having up to three substituents, especially up to two substituents, more especially none or a single substituent.

When either or both of A and $A^1$ are substituted phenyl or substituted naphthyl it is preferred that the substituents are independently selected from $C_{1-6}$-alkyl, $C_{1-6}$-alkoxy, phenyl, fluoro, chloro, bromo and $NR^1R^2$ wherein $R^1$ and $R^2$ are preferably each independently $C_{1-4}$-alkyl.

It is further preferred that the optional substituents on A and $A^1$ are independently selected from $C_{1-4}$-alkyl, $C_{1-4}$-alkoxy, chloro, bromo, fluoro, phenyl, $NHCOR^1$ and $CO_2R^1$, wherein $R^1$ is $C_{1-4}$-alkyl especially $C_{1-4}$-alkyl, $C_{1-4}$-alkoxy, Cl and Br. It is most preferred that the optional substituents on A and $A^1$ are independently selected from methyl, methoxy, chloro and bromo.

It is further preferred that A and $A^1$ are each independently selected from naphthyl and 4-methylphenyl and more especially that A is 4-methylphenyl and $A^1$ is naphth-2-yl.

A CGC used in known photosensitive element of electrophotographic devices is dibromoanthanthrone (DBA) as a CGC which has an absorption maxima in dimethyl formamide at 536 nm.

It has been found that compounds of the present invention have absorption maxima at longer wavelengths which more closely match the spectral output of lamps commonly used in electrophotographic devices. Thus the present compounds generally have a better photographic response than DBA in such devices.

Although the present compounds are beneficial on their own as CGCs, in admixture with DBA they provide compositions which can be used to extend the spectral response of a photosensitive element. The compositions may comprise a physical mixture of the compounds or a mixed crystal formed by co-precipitation of the two components from solution.

Extension of the spectral response is important in monochrome copying to enhance the intensity of black copies of originals printed in magenta through to green colours and in colour copying to give a more even response across the visible spectrum and thereby more faithful reproduction of the whole spectrum of colours.

The compounds of the present invention may generally be prepared by reacting an aromatic thiol with dibromoanthanthrone in the presence of a base. The reaction is preferably carried out in an organic aprotic solvent, by reacting the thiol with the base (from the thiol anion) followed by reaction with dibromoanthanthrone.

Symmetrical compounds, i.e. those in which A and $A^1$ are the same, may be prepared by reacting an excess of the appropriate thiol anion with DBA, preferably at least 2 moles/mole.

Unsymmetrical compounds can be prepared by reacting the DBA with at least 1 mole/mole of a first thiol, separating out the mono thiol adduct and then reacting this with at least 1 mole/mole of a second thiol. Alternatively, the DBA may be reacted with a mixture of the two thiols to give a mixture comprising two symmetrical adducts and one unsymmetrical adduct. Such mixtures may be used as CGC's in the form of a mixture or separated using known chromatographic techniques into the component compounds.

The compounds of Formula I and mixtures thereof can be used alone or in admixture with DBA in all proportions in place of DBA or any other CGC in the photosensitive element of an electrophotographic device.

The following examples are given as illustrations of the present invention.

EXAMPLE 1

Compound of Formula (1) wherein
$A=A^1=$4-methylphenyl

A mixture of p-thiocresol (10 g; 0.08 mol) and potassium hydroxide (5 g; 0.08 mol) in DMF (100 ml) was stirred at 60° C. in an ultrasonic bath for 1 hour. Dibromoanthanthrone (9.3 g; 0.02 mol) was then added and the mixture stirred for a further 1 hour at 60° C. The reaction mixture was cooled to 50° C. and added to methanol (1 liter). The resultant slurry was filtered and the solid washed with water and dried to give the title compound (9 g, 82%). λmax (DMF) 566 nm.

The compounds of Formula (1) in which A and $A^1$ are the same and have the meanings defined in the first column of Table 1 may be prepared by the method of Example 1, but in each case, replacing the 10 g p-thiocresol by 10 g of the thiol identified in the second column of Table 1.

TABLE 1

| Example | A = $A^1$ | Thiol |
|---|---|---|
| 2 | 3-methylphenyl | m-thiocresol |
| 3 | 2-methylphenyl | o-thiocresol |
| 4 | phenyl | thiophenol |
| 5 | 2-chlorophenyl | 2-chlorophenylthiol |
| 6 | 3-chlorophenyl | 3-chlorophenylthiol |
| 7 | 4-chlorophenyl | 4-chlorophenylthiol |
| 8 | 2-methoxyphenyl | 2-methoxyphenylthiol |
| 9 | 3-methoxyphenyl | 3-methoxyphenylthiol |
| 10 | 4-methoxyphenyl | 4-methoxyphenylthiol |
| 11 | 2,4-dichlorophenyl | 2,4-dichlorophenylthiol |
| 12 | 2,5-dichlorophenyl | 2,5-dichlorophenylthiol |

TABLE 1-continued

| Example | A = A¹ | Thiol |
|---|---|---|
| 13 | 2,6-dichlorophenyl | 2,6-dichlorophenylthiol |
| 14 | 2,4,6-trichlorophenyl | 2,4,6-trichlorophenylthiol |
| 15 | 3,4-dimethylphenyl | 3,4-dimethylphenylthiol |

EXAMPLE 16

Compound of Formula (1) wherein A=4-methylphenyl and A¹=naphth-2-yl

Stage I

A mixture of 2-thionaphthol (10 g; 0.06 mol) and potassium hydroxide (3.36 g; 0.06 mol) in DMF (100 ml) was stirred at 60° C. for 45 minutes. Dibromoanthanthrone (14.5 g; 0.03 mol) was then added and the mixture stirred at 60° C. for 2 hours. The reaction mixture was cooled to 50° C. and added to methanol (1 liter). The resultant slurry was filtered and the solid washed with water, dried to give a violet pigment (17.9 g; 92%), bromo(thionaphth-2-yl)-anthanthrone. λmax (DMF) 540 nm.

Stage II

A mixture of 4-thiocresol (4 g; 0.03 mol) and potassium hydroxide (1.8 g; 0.03 mol) in DMF (150 ml) was stirred at 60° C. for 1 hour. Bromo-(thionaphth-2-yl)anthanthrone (10 g; 0.016 mol) from Stage I was then added and the mixture stirred at 60° C. for 4 hours. The reaction mixture was cooled to 50° C. and added to methanol (1 liter). The resultant slurry was filtered and the solid washed with water, dried to give the title compound (8.45 g, 79%). λmax (DMF) 556 nm.

The compounds of Formula (1) in which A¹=-naphth-2-yl and A has the meaning defined in the first column of Table 2 may be prepared by the method of Example 16, in each case replacing the 4 g of 4-thiocresol by 4 g of the thiol identified in the second column of Table 2.

TABLE 2

| Example | A (A¹ = naphth-2-yl) | Thiol |
|---|---|---|
| 17 | 3-methylphenyl | m-thiocresol |
| 18 | 2-methylphenyl | o-thiocresol |
| 19 | phenyl | thiophenol |
| 20 | 2-chlorophenyl | 2-chlorophenylthiol |
| 21 | 3-chlorophenyl | 3-chlorophenylthiol |
| 22 | 4-chlorophenyl | 4-chlorophenylthiol |
| 23 | 2-methoxyphenyl | 2-methoxyphenylthiol |
| 24 | 3-methoxyphenyl | 3-methoxyphenylthiol |
| 25 | 4-methoxyphenyl | 4-methoxyphenylthiol |
| 26 | 2,4-dichlorophenyl | 2,4-dichlorophenylthiol |
| 27 | 2,5-dichlorophenyl | 2,5-dichlorophenylthiol |
| 28 | 2,6-dichlorophenyl | 2,6-dichlorophenylthiol |
| 29 | 2,4,6-trichlorophenyl | 2,4,6-trichlorophenylthiol |
| 30 | 3,4-dimethylphenyl | 3,4-dimethylphenylthiol |

The compounds of Formula (1) in which A¹ is phenyl and A has the meaning defined in the first column of Table 3 may be prepared by the method of Example 16, in each case replacing 2-thionaphthol by a molecular equivalent of phenylthiol, and replacing the 4 g of 4-thiocresol by 4 g of the thiol identified in the second column of Table 3.

TABLE 3

| Example | A (A¹ = phenyl) | Thiol |
|---|---|---|
| 31 | 3-methylphenyl | m-thiocresol |
| 32 | 2-methylphenyl | o-thiocresol |
| 33 | phenyl | thiophenol |
| 34 | 2-chlorophenyl | 2-chlorophenylthiol |
| 35 | 3-chlorophenyl | 3-chlorophenylthiol |
| 36 | 4-chlorophenyl | 4-chlorophenylthiol |
| 37 | 2-methoxyphenyl | 2-methoxyphenylthiol |
| 38 | 3-methoxyphenyl | 3-methoxyphenylthiol |
| 39 | 4-methoxyphenyl | 4-methoxyphenylthiol |
| 40 | 2,4-dichlorophenyl | 2,4-dichlorophenylthiol |
| 41 | 2,5-dichlorophenyl | 2,5-dichlorophenylthiol |
| 42 | 2,6-dichlorophenyl | 2,6-dichlorophenylthiol |
| 43 | 2,4,6-trichlorophenyl | 2,4,6-trichlorophenylthiol |
| 44 | 3,4-dimethylphenyl | 3,4-dimethylphenylthiol |

EXAMPLE 45

Compound of Formula (1) wherein A=3-methoxyphenyl and A¹=4-chlorophenyl

The method of Example 16 can be followed except that in place of 2-thionaphthol there is used an equivalent amount of 3-methoxyphenylthiol and in place of 4-thiocresol there is used an equivalent amount of 4-chlorophenylthiol.

We claim:

1. A compound of the formula:

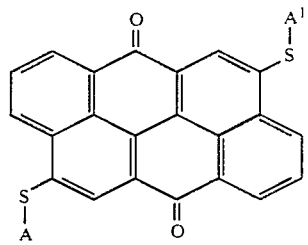

wherein
A is phenyl or substituted phenyl having up to three substituents selected from halo, $C_{1-6}$-alkyl and $C_{1-6}$-alkoxy;
A¹ is naphthyl or substituted phenyl having up to three substituents selected from halo, $C_{1-6}$-alkyl and $C_{1-6}$-alkoxy;
$R^1$ and $R^2$ are each independently H or $C_{1-6}$-alkyl.

2. A compound according to claim 1 in which the substituents are selected from $C_{1-4}$-alkyl or $C_{1-4}$-alkoxy.

3. A compound according to claim 1 in which the substituents are selected from methyl, methoxy, chloro and bromo.

4. A compound according to claim 1 in which A is 4-methylphenyl and A' is naphthyl or 4-methylphenyl.

5. A compound according to claim 1 in which A¹ is naphth-2-yl and A is 4-methylphenyl.

* * * * *